(12) United States Patent
Fast et al.

(10) Patent No.: US 10,499,647 B2
(45) Date of Patent: Dec. 10, 2019

(54) USE OF AN ENCAPSULATED CHLORINE BLEACH PARTICLE TO REDUCE GAS EVOLUTION DURING DISPENSING

(71) Applicant: Ecolab USA Inc., Saint Paul, MN (US)

(72) Inventors: Jonathan P. Fast, Shoreview, MN (US); John Nordling, St. Louis Park, MN (US)

(73) Assignee: Ecolab USA Inc., Saint Paul, MN (US)

( * ) Notice: Subject to any disclaimer, the term of this patent is extended or adjusted under 35 U.S.C. 154(b) by 0 days.

(21) Appl. No.: 15/402,736

(22) Filed: Jan. 10, 2017

(65) Prior Publication Data

US 2018/0192643 A1   Jul. 12, 2018

(51) Int. Cl.
*A01N 59/00*   (2006.01)

(52) U.S. Cl.
CPC .................................. *A01N 59/00* (2013.01)

(58) Field of Classification Search
None
See application file for complete search history.

(56) References Cited

U.S. PATENT DOCUMENTS

| | | | |
|---|---|---|---|
| 2,815,311 A | 12/1957 | Ellis et al. | |
| 4,557,926 A | 12/1985 | Nelson et al. | |
| 4,681,914 A | 7/1987 | Olson et al. | |
| 4,916,153 A | 4/1990 | Bain et al. | |
| 5,015,643 A | 5/1991 | Jones et al. | |
| 5,141,664 A | 8/1992 | Corring et al. | |
| 5,208,057 A | 5/1993 | Greenley et al. | |
| 5,464,636 A | 11/1995 | Hight et al. | |
| 5,688,515 A | 11/1997 | Kuechler et al. | |
| 5,834,414 A | 11/1998 | Sowle et al. | |
| 6,262,013 B1 | 7/2001 | Smith et al. | |
| 7,285,522 B2 | 10/2007 | Van Buskirk | |
| 7,488,708 B2 | 2/2009 | Deljosevic et al. | |
| 8,894,898 B2 | 11/2014 | Stolle et al. | |
| 9,139,800 B2 | 9/2015 | Monsrud et al. | |
| 9,288,982 B2 | 3/2016 | McSherry et al. | |
| 2003/0059483 A1 | 3/2003 | Sowle et al. | |
| 2006/0088498 A1 | 4/2006 | Martin et al. | |
| 2006/0197058 A1* | 9/2006 | Martin | A01N 37/42 252/188.1 |
| 2009/0148342 A1 | 6/2009 | Bromberg et al. | |
| 2010/0183693 A1 | 7/2010 | Martin | |
| 2012/0285693 A1 | 11/2012 | Mirakyan et al. | |
| 2013/0101478 A1* | 4/2013 | Johnson | B01F 5/0496 422/261 |

FOREIGN PATENT DOCUMENTS

| | | |
|---|---|---|
| AU | 2004240145 A1 | 6/2005 |
| WO | 2010017405 A1 | 2/2010 |

OTHER PUBLICATIONS

XP-002778654, WPI 2017 Clarivate Analytics, pp. 1-4. 2017.
European Patent Office, "Notification of Transmittal of the International Search Report and the Written Opinion of the International Searching Authority, or the Declaration," in connection to PCT/US2018/012319, filed Jan. 4, 2018, 15 pages, dated Mar. 12, 2018.

* cited by examiner

*Primary Examiner* — David J Blanchard
*Assistant Examiner* — Daniel F. Coughlin
(74) *Attorney, Agent, or Firm* — McKee, Voorhees & Sease, PLC

(57) ABSTRACT

The present disclosure relates to use of an encapsulated chlorine bleach to reduce gas evolution when reacted with sodium bromide during dispensing. The compositions include a coated chlorine combined with the sodium bromide which beneficially suppresses the chemical reaction, and therefore gas release, while providing a single, solid, all-in-one composition. Compositions, methods of dispensing and methods of use are disclosed.

13 Claims, No Drawings

USE OF AN ENCAPSULATED CHLORINE BLEACH PARTICLE TO REDUCE GAS EVOLUTION DURING DISPENSING

FIELD OF THE INVENTION

The present disclosure relates to the use of an encapsulated chlorine bleach to reduce gas evolution when reacted with sodium bromide during dispensing. More particularly, a solid bromine biocide is provided and the amount of gas released when exposed to liquid and/or moisture is significantly decreased through the use of an encapsulated chlorine bleach.

BACKGROUND OF THE INVENTION

Chlorine biocides are widely adapted and used due to its various applications and advantages. However, chlorine biocides have disadvantages which are widely recited both in the literature and in the patent art. Bromine biocides have numerous conventional applications and are considered the "gold standard" for cooling towers, due to its many advantages over chlorine. These benefits of bromine chemistry in comparison to chlorine include, but are not limited to: enhanced performance at alkaline pH values above 7.5; enhanced performance in the presence of ammonia and other nitrogenous materials; and enhanced performance against biofilms, i.e. bacteria residing on surfaces rather than in solution. Accordingly, bromine biocides are particularly useful in controlling biofouling.

Typically, bromine biocides perform their functions through hypobromous acid (HOBr), which in turn is usually formed by reacting chlorine bleach (either hypochlorous acid (HOCl) or hypochlorite (NaOCl)) with sodium bromide (NaBr). Chlorine bleach solution can be mixed with sodium bromide solution, although the two components must be kept separate until mixing or immediately before the bromine biocide application as it is known that combining the two solutions (chlorine and sodium bromide) are highly reactive. U.S. Pat. No. 5,464,636 discloses the separate feeding of solutions for generating a biocide for use in a cooling tower through the use of separate chlorine and bromine feeders. The conventional generation inherently possesses numerous health, safety and/or environmental concerns.

Solid compositions of both chlorine and sodium bromide are available and benefit an end user by only needing one product rather than two separate liquid solutions. Such solid products containing both chlorine and sodium bromide are known; however the dispensing disadvantage of stability and control over the safety of the reaction to generate the bromine biocide present challenges for use of this solid technology.

Stable solid disinfectant compositions, disclosed in U.S. Pat. No. 2,815,311 to the Diversey Corporation in 1957, is an early example of a solid bromine biocide composition. Further advances throughout the years have been focused on improving the stability of the chlorine and NaBr combination. Other patents that describe a tablet containing a combination of a chlorine species with a bromide ion source include U.S. Pat. Nos. 4,557,926 and 5,015,643.

U.S. Pat. No. 5,688,515 to Occidental Chemical Corporation in 1997 claims a method for increased stability for a combination of trichloroisoyanuric acid and sodium bromide. Using such product for a small recirculating water system, an operator usually adds one or more disinfectant tablets by hand into the water system, and the added tablets are submerged into a bulk of water. With enough water around the tablets, the reaction between trichloroisoyanuric acid and sodium bromide forms hypobromous acid (HOBr) as the three reactions shown below proceed to the desired product.

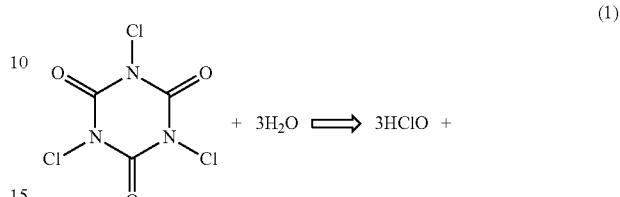

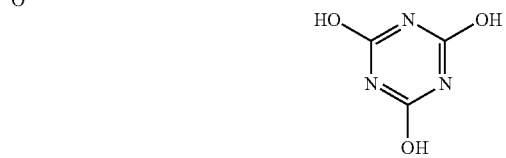

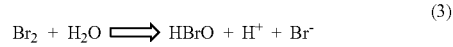

Using such product for larger cooling towers, putting the tablets or blocks into the bulk water becomes impractical and not desirable, thus an automated feeder or dispenser is preferred. However, there exists a need for improved dispensing and dosing of the biocide. In such a feeder, the tablets must be wetted and dissolved prior to introduction into the cooling water stream. It is in those feeders, the reaction between trichloroisoyanuric acid and sodium bromide generates both bromine gas and HOBr. This is distinct from adding such a tablet (or other solid) directly into bulk water, as in such direct addition to bulk water the large excess of water will drive the reaction to produce more HOBr. In such a reaction there is excess water to solubilize any newly formed bromine gas, which is distinct from the dispenser where less water is present and therefore less capability to solubilize the formed bromine gas.

Bromine gas is a noxious, pungent smelling, reddish-brown gas. The gas can lead to severe corrosion of equipment. In addition, the gas is a health hazard to personnel operating the blending and tableting units, and still further the produced gas could cause an explosion if generated in sufficient quantities under pressure.

U.S. Pat. No. 5,688,515 acknowledged drawback of the potential for significant gas release when a tablet is wetted and the consequences as the result of it. The reference teaches that moisture adversely affects the water stability of tablets or solid compositions of chlorine and sodium bromide. Moisture causes a reaction to occur between the trichloroisocyanuric acid and sodium bromide particles which results in the formation of bromine gas.

Other approaches have been used to prevent HBrO to escape once it has been formed. For example, U.S. Pat. No. 5,464,636 discloses the combination of either trichloro- or dichloro-isocyanuric acid together with sodium bromide. It is stated that once the chlorine and bromine species react in situ to form hypobromous acid (HOBr), that newly formed HOBr can evaporate from the recirculating water system. The authors seek to limit the evaporation of the HOBr from the use solution by the addition of a "bromine volatilization suppressant." However, the disclosed method is to prevent evaporation from the use solution and does not address gas release from the solid product during the dispensing process.

Despite the various approaches taken to solve the problem associated with dispensing a solid composition to produce the bromine biocide HBrO, this problem remains unsolved. Thus, using a product that contains both chlorine bleach (either hypochlorous acid (HOCl), hypochlorite (NaOCl), or precursor thereof) and sodium bromide (NaBr) in water towers presents opportunities for enhanced safety and conditions for operation.

Accordingly, it is the objective of this invention to reduce the amount of bromine gas produced by using a chlorine bleach and bromide product in water towers.

It is a further objective of the claimed disclosure to provide a dispensing mechanism for reducing the amount of gas evolution when reacting sodium bromide with chlorine.

A further object of the disclosure is to produce stable and safe solid biocides for various applications of use.

Other objects, advantages and features of the present disclosure will become apparent from the following specification taken in conjunction with the accompanying drawings.

BRIEF SUMMARY OF THE INVENTION

An advantage of the disclosure is a solid chlorine and sodium bromide compositions suitable for reducing gas generation upon dispensing thereof. In an beneficial aspect, the compositions, methods of dispensing the compositions and methods of employing the same reduce the concentration of bromine gas generated by at least 2 times compared to the concentration of bromime gas generated by a non-coated chlorine reagent, or at least 3 times, or at least 4 times, or at least 5 times, or at least 6 times, or at least 7 times, or at least 8 times, or at least 9 times, or at least 10 times, thereby enhancing the safety of the dispensing and use of the bromine biocides. A further advantage of the disclosure is the stable, solid chlorine and sodium bromide composition for on-site or at a point of use generation of sodium bromine.

In an aspect, a method of dispensing a solid biocide comprises providing a solid biocide composition to a dispenser, wherein the composition comprises a coated chlorine and sodium bromide; contacting the solid biocide composition with a water source to initiate the reaction between chlorine and sodium bromide at a wet interface on the solid biocide composition; and generating hypobromous acid and/or sodium hypobromite while reducing the concentration of bromine gas generated at the wet interface and remaining in the dispenser.

In an aspect, a solid, all-in-one biocide composition comprises a coated chlorine; and sodium bromide.

These and other objects, features, and/or advantages of the disclosure will be apparent to those skilled in the art. The disclosure is not to be limited to or by these objects, features, and/or advantages. No single embodiment need provide each and every object, feature, and/or advantage. While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

DETAILED DESCRIPTION OF THE INVENTION

The embodiments of this disclosure are not limited to particular applications of use of the bromine biocide composition for in situ generation, which can vary and are understood by skilled artisans based upon the disclosure of the invention herein. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers within the defined range. Throughout this disclosure, various aspects of this disclosure are presented in a range format. It should be understood that the description in range format is merely for convenience and brevity and should not be construed as an inflexible limitation on the scope of the disclosure. Accordingly, the description of a range should be considered to have specifically disclosed all the possible sub-ranges as well as individual numerical values within that range (e.g. 1 to 5 includes 1, 1.5, 2, 2.75, 3, 3.80, 4, and 5).

So that the present disclosure may be more readily understood, certain terms are first defined. Unless defined otherwise, all technical and scientific terms used herein have the same meaning as commonly understood by one of ordinary skill in the art to which embodiments of the disclosure pertain. Many methods and materials similar, modified, or equivalent to those described herein can be used in the practice of the embodiments of the present disclosure without undue experimentation, the preferred materials and methods are described herein. In describing and claiming the embodiments of the present disclosure, the following terminology will be used in accordance with the definitions set out below.

The term "about," as used herein, refers to variation in the numerical quantity that can occur, for example, through typical measuring (e.g. time, temperature, pH) and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

As used herein, the term "biocide" refers to agents such as germicides, bactericides, disinfectants, sterilizers, preservatives, fungicides, algicides, aquaticides, herbicides, insecticides, larvicides, pesticides, plant growth regulators and the like, each of which may be used for their ability to inhibit growth of and/or destroy various biological and/or microbiological species such as bacteria, fungi, algae, insects, larvae, worms and the like.

The term "actives" or "percent actives" or "percent by weight actives" or "actives concentration" are used interchangeably herein and refers to the concentration of those ingredients involved in cleaning expressed as a percentage minus inert ingredients such as water or salts.

As used herein, the term "cleaning" refers to a method used to facilitate or aid in soil removal, bleaching, microbial population reduction, and any combination thereof. As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

As used herein, the term "disinfectant" refers to an agent that kills all vegetative cells including most recognized pathogenic microorganisms, using the procedure described in *A.O.A.C. Use Dilution Methods*, Official Methods of Analysis of the Association of Official Analytical Chemists, paragraph 955.14 and applicable sections, 15th Edition, 1990 (EPA Guideline 91-2). As used herein, the term "high level disinfection" or "high level disinfectant" refers to a compound or composition that kills substantially all organisms, except high levels of bacterial spores, and is effected with a chemical germicide cleared for marketing as a sterilant by the Food and Drug Administration. As used herein, the term "intermediate-level disinfection" or "intermediate level disinfectant" refers to a compound or composition that kills mycobacteria, most viruses, and bacteria with a chemical germicide registered as a tuberculocide by the Environmental Protection Agency (EPA). As used herein, the term "low-level disinfection" or "low level disinfectant" refers to a compound or composition that kills some viruses and bacteria with a chemical germicide registered as a hospital disinfectant by the EPA.

For the purpose of this patent application, successful microbial reduction is achieved when the microbial populations are reduced by at least about 50%, or by significantly more than is achieved by a wash with water. Larger reductions in microbial population provide greater levels of protection.

As used herein, the term "sanitizer" refers to an agent that reduces the number of bacterial contaminants to safe levels as judged by public health requirements. In an embodiment, sanitizers for use in this disclosure will provide at least a 3 log reduction and more preferably a 5-log order reduction. These reductions can be evaluated using a procedure set out in *Germicidal and Detergent Sanitizing Action of Disinfectants*, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, 25±2° C., against several test organisms.

As used herein, the term "soil" or "stain" refers to a non-polar oily substance which may or may not contain particulate matter such as mineral clays, sand, natural mineral matter, carbon black, graphite, kaolin, environmental dust, etc.

As used herein, a "solid composition" refers to a composition in the form of a solid for example, as a powder, a flake, a granule, a pellet, a tablet, a lozenge, a puck, a briquette, a brick, a solid block, or a unit dose. According to a preferred embodiment, a solid is a tablet, puck, brick or block enabling multiple uses or dispensing. The term "solid" refers to the state of the composition under the expected conditions of storage and dispensing for use of the solid composition to generate a bromine biocide according to the disclosure herein. In general, it is expected that the solid biocide composition will remain in solid form when exposed to temperatures of about 120° F., or greater.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbistatic. A sanitizer and a disinfectant are, by definition, agents which provide antimicrobial or microbiocidal activity. In contrast, a preservative is generally described as an inhibitor or microbistatic composition As used herein, the term "treatment", or "treating", refers to any use of the generated biocide in conjunction with a desired function and/or for a desired purpose. The term "treatment", or "treating", does not imply any particular action by the fluid.

As used herein, the term "substantially free" refers to compositions completely lacking the component or having such a small amount of the component that the component does not affect the performance of the composition. The component may be present as an impurity or as a contaminant and shall be less than 0.5 wt-%. In another embodiment, the amount of the component is less than 0.1 wt-% and in yet another embodiment, the amount of component is less than 0.01 wt-%. The term "free" refers to compositions completely lacking the component.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The methods and compositions of the present disclosure may comprise, consist essentially of, or consist of the components and ingredients of the present disclosure as well as other ingredients described herein. As used herein, "consisting essentially of" means that the methods and compositions may include additional steps, components or ingredients, but only if the additional steps, components or ingredients do not materially alter the basic and novel characteristics of the claimed methods, systems, apparatuses, and compositions.

It should also be noted that, as used in this specification and the appended claims, the term "configured" describes a system, apparatus, or other structure that is constructed or configured to perform a particular task or adopt a particular configuration. The term "configured" can be used interchangeably with other similar phrases such as arranged and configured, constructed and arranged, adapted and configured, adapted, constructed, manufactured and arranged, and the like.

Solid Biocide

In an aspect, the solid biocide comprises a coated chlorine and a sodium bromide. A solid composition processed according to the method of the disclosure can be substantially homogeneous with regard to the distribution of ingredients throughout its mass and is dimensionally stable.

In an aspect, the solid biocide composition provides the beneficial effect of gas suppression at the point of dispensing, namely where the multi-use solid composition has remaining chemistry for subsequent dosing and dispensing. This is distinct from various applications in the art where encapsulation or other stabilization techniques are employed for bromine gas suppression when the product (liquid or solid) is added to a main water source or an point of use; instead according to the description herein the bromine gas suppression refers to the solid biocide composition remaining in the package or dispenser. This is critical for a multi-use composition as the remaining composition does not stay dry (i.e. prevent further chemical reaction following exposure to water). Prior art assumes that a package or a composition will remain separate (and not in contact until the point of use), such as disclosed in U.S. Pat. No. 5,464,636, which is not possible for multi-use compositions remaining in a dispenser.

According to the present disclosure gas suppression is achieved by the coated chlorine combined in a solid with the sodium bromide, as opposed to a bulk solution. In a dispenser containing a multi-use solid biocide composition according to the disclosure, there is water residue left behind at the interface of a freshly dispensed block, or the wet interface, as referred to herein. At such wet interface the solid biocide composition will continue to react and continue to produce gas until the surface is completely dry. The solid biocide composition disclosed herein slows the gas evolution as a result of the physical barrier provided by the coated chlorine. In an aspect, the gas evolution is slowed by at least 2 times, or at least 3 times, or at least 4 times, or at least 5 times, or at least 6 times, or at least 7 times, or at least 8 times, or at least 9 times, or at least 10 times, thereby enhancing the safety of the dispensing and use of the bromine biocides. The reduction of the gas evolution is critical as the gas continues to build up in the dispenser well after the particular dispense cycle has finished. According to the invention, use of coated chlorine in the solid biocide composition substantially slows the reaction, and therefore gas production, at the wet interface of the block until it is dry.

Coated Chlorine

In an aspect, the coated chlorine for the solid biocide composition provides a physical barrier for the chlorine. The reference to the physical barrier can refer to a coating, encapsulation or the like. In an aspect, the physical barrier prevents the deleterious premature reaction of the chlorine with the sodium bromide. In an aspect, the coated chlorine suppresses the reaction to generate hypobromous acid which would cause a loss in the active titration level of the chlorine and potentially degradation of other ingredients in the solid biocide composition. Moreover, the coated chlorine therefore gas release, while allowing a solid all-in-one composition.

Exemplary coated chlorine sources include for example, chloroisocyanurate, trichloroisocyanuric acids and dichloroisocyanuric acids and salts thereof, including dichloroisocyanurate and trichloroisocyanurate. As one skilled in the art will ascertain, the amount of available chlorine in the various chlorine sources (i.e. the base chlorine before it is coated) vary dependent upon the structure. In an aspect, the coated chlorine for use in the solid biocide composition has at least 50% available chlorine in the base chlorine (e.g. dichlorisocyanurate having 56% available chlorine), or in some embodiments at least about 90% available chlorine in the base chlorine (e.g. trichloroisocyanurate having 90% available chlorine).

The coated chlorine may employ additional coatings or encapsulates. In an embodiment an additional coating may be employed, including for example sulfates, such as sodium sulfate or sodium tripolyphosphate.

Additional description of suitable encapsulated or coated chlorine/halogen bleaches is set forth in U.S. Pat. No. 4,681,914, the entire contents of which are herein incorporated by reference.

Still further description of suitable encapsulated or coated chlorine bleaches include those wherein the encapsulated bleach is further formulated into a solid block product. Exemplary active halogen releasing bleaches are disclosed, for example, in U.S. Pat. Nos. 4,830,773, 4,731,195 and 4,657,784, the entire contents of which are herein incorporated by reference. A non-limiting list of such bleaches includes active halogen releasing bleaches such as hypochlorites, chlorites, chlorinated phosphates, chloroisocyanates, chloroamines etc.; and peroxide compounds such as hydrogen peroxide, perborates, percarbonates etc. Preferred bleaches include those bleaches which liberate an active halogen species such as Cl—, Br—, OCl—, or OBr— under conditions normally encountered in typical cleaning processes. Most preferably, the bleaching agent releases Cl— or OCl—. A non-limiting list of useful chlorine releasing bleaches includes calcium hypochlorite, lithium hypochlorite, chlorinated trisodium phosphate, sodium dichloroisocyanurate, potassium dichloroisocyanurate, [(monotrichloro)-tetra(monopotassium dichloro)]pentaisocyanurate, monochloroamine, dichloroamine, trichloromelamine, sulfondichloro-amide, 1,3-dichloro-5,5-dimethylhydantoin, n-chloroammeline, n-chlorosuccinimide, n,n'-dichloroazodicarbonimide, n,n-chloroacetyl urea, n,n'-dichlorobiuret, chlorinated dicyanamide, trichlorocyanuric acid, and hydrates thereof. As disclosed therein, the bleach may be encapsulated in any convenient manner capable of ensuring complete coating of the bleach. For reasons of low manufacturing cost and ease of manufacture the bleach is preferably encapsulated in a fluidized bed. Briefly, the separating composition is dissolved in an appropriate solvent, such as water when water soluble, to form an inner coating solution; the water soluble cellulose ether dissolved in water to form an outer coating solution; the bleach particles fluidized in a fluidized bed apparatus, the inner coating solution sprayed onto the fluidized particles and dried, and the outer coating solution sprayed on the fluidized particles and dried.

Bromide Salts

In an aspect, the bromide is provided as a bromide salt, namely an alkali metal salt. In an aspect, the bromide salt is sodium bromide provided in the solid composition to react with the chlorine to generate the bromine biocide according to the disclosure. In an aspect, the bromide salt is potassium bromide provided in the solid composition to react with the chlorine to generate the bromine biocide according to the disclosure.

Additional Functional Ingredients

In some embodiments, the solid biocide compositions can include other additional functional ingredients. Additional functional ingredients suitable for use with the solid biocide compositions can include, but are not limited to, corrosion inhibitors, acidulants, stabilizing agents, e.g., chelating agents, sequestrants, threshold agents, buffers, detergents, thickeners, foaming agents, solidification agents, aesthetic enhancing agents (i.e., colorants, odorants, or perfumes) and other active agents.

Additional Biocides

The solid compositions can further comprise and/or be combined at a point of use with additional biocides.

Examples of suitable biocides may include both non-oxidizing and oxidizing biocides. Examples of commonly available oxidizing biocides include hypochlorite bleach, such as calcium hypochlorite and lithium hypochlorite, peracetic acid, chlorine dioxide, ozone, inorganic persulfates such as ammonium persulfate, or peroxides, such as hydrogen peroxide and organic peroxides, potassium monopersulfate, potassium peroxymonosulfate, bromochlorodimethylhydantoin, dichloroethylmethylhydantoin, or chlorinated hydantoins.

Examples of commonly available non-oxidizing biocides may include quaternary ammonium salts, aldehydes and quaternary phosphonium salts, dibromonitfilopropionamide, thiocyanomethylthiobenzothlazole, methyldithiocarbamate, tetrahydrodimethylthladiazonethione, tributyltin oxide, bromonitropropanediol, bromonitrostyrene, methylene bisthiocyanate, chloromethylisothlazolone, methylisothiazolone, benzisothlazolone, dodecylguanidine hydrochloride, polyhexamethylene biguanide, tetrakis(hydroxymethyl)phosphonium sulfate, glutaraldehyde, alkyldimethylbenzyl ammonium chloride, didecyldimethylammonium chloride, poly [oxyethylene-(dimethyliminio)ethylene(dimethyliminio)ethylene dichloride], decylthioethanamine, and terbuthylazine.

Additional disclosure of biocides suitable for combination according to the invention, including for example, U.S. Pat. No. 9,371,479, which is herein incorporated by reference in its entirety.

Hardening Agents

The solid compositions can further comprise a hardening agent. The solid compositions can include a variety of solidification agents or hardening agents.

Exemplary Formulations

The solid biocide compositions as disclosed herein can be formulated as shown in Table 1.

TABLE 1

| Material | First Exemplary Range wt-% | Second Exemplary Range wt-% | Third Exemplary Range wt-% |
|---|---|---|---|
| Coated chlorine | 70-99 | 85-99 | 90-99 |
| Sodium bromide | 1-30 | 1-15 | 1-10 |
| Additional functional ingredient(s) | 0-50 | 0.01-40 | 0.1-40 |

The solid biocides may be used in various applications, such as preventing and removing biofouling in recirculating waters, cooling towers, and the like. The solid biocide is suitable to eliminate any number of living organisms, such as bacteria found in such biofouling. Furthermore, biocides may include a basic to acidic pH range and thus be effective and function at a pH of from about 6 to about 12, in embodiments from about 7 to about 10, or from about 8 to about 9. The solid biocide composition may take forms including, but not limited to: a solid pellet, block, tablet, powder, granule, flake, lozenge, a puck, a briquette, a brick, a solid block, or a unit dose. In an exemplary embodiment, solids may have a weight of approximately 100 grams or greater, 250 grams or greater, 500 grams or greater, 750 grams or greater, or solid blocks may also have a mass of between approximately 1 and approximately 10 kilograms. In certain embodiments, the solid composition are provided in the form of a unit dose. A unit dose refers to a solid detergent composition unit sized so that the entire unit is used during a single washing cycle. When the solid cleaning composition is provided as a unit dose, it can have a mass of about 1 g to about 50 g. In other embodiments, the composition can be a solid, a pellet, or a tablet having a size of about 50 g to 250 g, of about 100 g or greater, or about 1 kg and 10 kg.

In other embodiments, the solid detergent composition is provided in the form of a multiple-use solid, such as, a block, and can be repeatedly used to generate aqueous biocide compositions for multiple applications of use. In certain embodiments, the solid composition is provided as a solid having a mass of about 5 g to 10 kg. In certain embodiments, a multiple-use form of the solid composition has a mass of about 1 to 10 kg. In further embodiments, a multiple-use form of the solid composition has a mass of about 5 kg to about 8 kg. In other embodiments, a multiple-use form of the solid composition has a mass of about 5 g to about 1 kg, or about 5 g and to 500 g.

In an aspect, the solid biocide composition is a pressed solid. In an embodiment a pressed solid according to the present disclosure contains a small enough amount of a liquid, such as water, such that compressing the powder or solid components at several hundred psi does not squeeze liquid from the solid. In an aspect, the flowable solids suitable for pressing can be a powder or a wetted powder. In an aspect, the composition to be pressed comprises less than about 12 wt-% liquid, less than about 10 wt-% liquid, less than about 5 wt-% liquid, less than about 1 wt-% liquid, or less than about 0.5 wt-% liquid. In other aspects, the composition to be pressed comprises between about 0.5 wt-% to about 12 wt-% liquid, 1 wt-% to about 12 wt-% liquid, or preferably between about 2 wt-% to about 12 wt-% liquid.

Pressing can employ low pressures compared to conventional pressures used to form tablets or other conventional solid detergent compositions. For example, in an embodiment, the present method employs a pressure on the solid of less than or equal to about 10,000 pounds per square inch (psi), less than or equal to about 7,500 psi, or less than or equal to about 5,000 psi. The method of the present disclosure can produce a stable solid without employing a melt and solidification of the melt as in conventional casting. Forming a melt requires heating a composition to melt it. The heat can be applied externally or can be produced by a chemical exotherm (e.g., from mixing caustic (sodium hydroxide) and water). Heating a composition consumes energy. Handling a hot melt requires safety precautions and equipment. Further, solidification of a melt requires cooling the melt in a container to solidify the melt and form the cast solid. Cooling requires time and/or energy. The solids of the present disclosure are held together not by solidification from a melt but by a combination of compression and functional components disposed therein.

In some aspects the pressed solid is cured for a period of time. In other aspects, the pressed solid does not require curing. In aspects where the composition is cured, the amount of time the compositions are cured depends on a variety of factors, including, but not limited to, the desired rigidity of the solid composition, the ingredients present in the solid, and the desired end use of the solid. In some embodiments, the compositions are cured for at least about 30 minutes, at least about 1 hour, at least about 1 day, or at least about 1 week. In other embodiments, the compositions are cured for about 15 to about 30 minutes. The compositions are cured at ambient temperature. That is, the compositions do not require heating or cooling during the cure step.

Methods of Dispensing and Use

The solid biocide compositions according to the present disclosure are suitable for use in various biocidal applications. In an exemplary aspect, the solid biocide composition provides hypobromous acid for use in preventing biofouling in various applications. In a particular aspect, the generated biocide is particularly well suited for use in cooling towers. In other aspects, the generated biocide is particularly well suited for use in treatment of other industrial water systems operating at alkaline pH.

The dispensing of the solid biocide composition according to the disclosure can be achieved through various commercially-available dispensers. Preferably the dispenser is an external dispenser. As referred to herein, an external dispenser provides a solid product into a dispenser that is physically separated from a main water system. In such an external dispenser the released gas has less water to dissolve as the unit is physically smaller and presents the challenge of pressure buildup from generated gas; moreover solid product remains in the dispenser as intended for subsequent dosing and is therefore capable of evolving gas. Conversely, if a solid product is added directly to a main water system, then only enough product for a single dose is added. Such systems are not considered external dispensers as the solid composition (e.g. puck or tablet) is added directly to a main water system, gas release doesn't matter as much as there is a large volume of water to solubilize the generated gas thereby making any gas release more diffuse (and not localized in a particular spot); moreover the system size is much bigger (and often open) to accommodate any gas release without pressure buildup.

Suitable examples include various spray on dispensers. Further suitable examples include inverted T dispensers. In general, dispensing systems include a means for dosing water (or suitable diluent) onto the solid biocide composition, a container our housing for the solid biocide composition, and a fluid delivery system. In an aspect, the dispenser is configured to spray, flow or otherwise contact water (or suitable diluent) onto the solid biocide composition. The configuration may include a pump, spray nozzle, tubing or the like, which may further include electronically actuatable delivery valves and/or controllers configured to control application of the water dosing. In an aspect, the solid biocide composition is housed within a reservoir within a dispensing system for the intermittent generation and dosing of the bromine biocide. In an aspect, the water is added in a periodic or intermittent fashion through a step of turning on and off a water source. In an aspect, water can be added for a period of a few seconds to a few minutes, or from about 30 seconds to about 5 minutes, or from about 30 seconds to about 4 minutes, or from about 1 minute to about 3 minutes. After contacting the solid biocide composition an aqueous solution thereof is passed into a fluid delivery system, such as a water stream for dispensing the biocide generated therefrom. The dispensing of the biocide composition according to the disclose is distinct from a solid composition in constant contact with a water source, e.g. solid puck added into a aqueous tank or a product dispensed directly into the bulk water system. The intermittent or period dosing of the solid biocide composition presents difficulties in needing to prolong or stop the reaction of the chlorine and the sodium bromide at a wet interface to prevent buildup of gas generated from the reaction of the chlorine and sodium bromide, which is beneficially achieved according to the disclosure by a significant reduction in the gas evolution. Whether the solid biocide composition continuously maintains a wet interface (or completely dries) will depend upon multiple factors, e.g. surface area of the solid biocide composition and frequency of the contacting of the composition with water.

The dispensing systems suitable for use according to the invention preferably has a fluid delivery system configured below the reservoir, e.g. a bottom tube running perpendicular to the direction of the water flow to the solid composition in the reservoir, such as in an inverted T design. In an aspect, there is a constant low level of water flowing thereunder the reservoir housing the solid biocide composition through the fluid delivery system. Beneficially the constant flow of water beneath the reservoir housing the solid composition allows for any gas generated from the ongoing reaction of the solid biocide composition at the wet interface of the solid biocide composition to be pulled into the water stream, i.e. an aspirator. This is particularly beneficial as the solid biocide composition having a wet interface will have some amount of reacting chemistry and causing ongoing gas evolution until the solid composition is dry. One skilled in the art will appreciate that with intermittent addition of water (e.g. spray or flow) to the solid biocide composition there may be extended periods of time where a wet interface of the solid biocide composition is present. The removal of gas vapors generated from the reaction of the chlorine and sodium bromide into the water stream, i.e. aspirator, prevents buildup of the gas within the housing reservoir for the solid biocide composition or from leaking out from such housing into the surrounding environment and presenting dangerous conditions and/or building of pressure within a system which could result in an explosion of the system absent a release of such pressure. Beneficially, the gas can be physically removed from the system itself.

In an aspect, the dosing system is a closed system such that no venting of the bromine gas occurs. This beneficially reduces the environmental and safety concerns associated with the gasing off from the reaction of the solid biocide composition.

In an aspect, the use of the solid biocide composition described herein results in the gas evolution reduced or slowed by at least 2 times, or at least 3 times, or at least 4 times, or at least 5 times, or at least 6 times, or at least 7 times, or at least 8 times, or at least 9 times, or at least 10 times, thereby enhancing the safety of the dispensing and use of the bromine biocides. According to the disclosure, use of coated chlorine in the solid biocide composition substantially slows the reaction, and therefore gas production, at the wet interface of the solid composition.

In an aspect, the solid biocide composition is suitable for generating and dosing any desired concentration of the bromine biocide. In an aspect, the compositions and methods generate at least about 1 ppm, at least about 10 ppm, at least about 100 ppm, at least about 500 ppm, at least about 1,000 ppm, at least about 5,000 ppm, at least about 10,000 ppm, at least about 20,000 ppm, at least about 50,000 ppm, or greater for dosing into an application of use.

All publications and patent applications in this specification are indicative of the level of ordinary skill in the art to which this invention pertains. All publications and patent applications are herein incorporated by reference to the same extent as if each individual publication or patent application was specifically and individually indicated as incorporated by reference.

EXAMPLES

Embodiments of the present invention are further defined in the following non-limiting Examples. It should be understood that these Examples, while indicating certain embodiments of the disclosure, are given by way of illustration only. From the above discussion and these Examples, one skilled in the art can ascertain the essential characteristics of this disclosure, and without departing from the spirit and scope thereof, can make various changes and modifications of the embodiments of the disclosure to adapt it to various usages and conditions. Thus, various modifications of the embodiments of the disclosure, in addition to those shown and described herein, will be apparent to those skilled in the art from the foregoing description. Such modifications are also intended to fall within the scope of the appended claims.

Example 1

An experiment was designed to systematically evaluate and measure the generation of bromine gas from the reaction of chlorine and sodium bromide. The measurement of gas evolution was from a single one puck using a Porta Sens II gas detector. The Porta Sens II detector has removable or adjustable sensor modules and for this test a chlorine sensor (00-1003) with a detection range from about 5 ppm to about 200 ppm was used. Importantly, the sensor is unable to discriminate between halogenated oxidant gases; so the sensor will detect bromine gas in addition to chlorine.

One puck (75 grams) of each test chemistry (Coated Chlorine/NaBr and uncoated product Uncoated Chlorine/NaBr) was used. The puck was placed in the center of a bottom spray dispenser. A hole was cut into the side of the chamber and the probe was inserted directly into the compartment, to read gas evolution in real time. To dispense, cold water was sprayed at 1 gallon per minute for 2 minutes with the lid of the dispenser closed. The gas output after spray-on dispensing of two different test systems measured with a Porta Sens gas detector can be seen below in Table 1.

TABLE 1

Gas output

| | Amount of $Br_2$ (ppm) | | |
|---|---|---|---|
| Time (min) | Coated Chlorine/NaBr | Uncoated Chlorine/NaBr | |
| 0 | 0 | 0 | |
| 1 | 1.8 | 2 | |
| 2 | 2.6 | 3.2 | |
| 3 | 6.4 | 7.2 | |
| 5 | 18.8 | 35.3 | |
| 7 | 30.7 | 61.3 | |
| 10 | 39.3 | 100.2 | |
| 12 | 40 | 121.2 | |
| 15 | 39 | 149.8 | |
| 18 | 36.4 | 167.8 | |
| 21 | — | 180.6 | |
| 23 | — | 185.2 | |
| 25 | — | 186.8 | |
| 27 | — | 186.4 | |
| 29 | — | 185.8 | |
| 33 | — | 179.3 | Multiplier |
| Average of 3 peak points | 39.4 | 186.1 | 4.7 |

Typically, during the initial 2 minute dispense time the flow of water down the bottom hose provides a suction force to pull the produced vapors down. Given that, the rate starts to increase after 2 minutes. After the initial 2 minute wetting time, gas will continue to evolve until the puck is dry, at which point a plateau level will be reached. Once the plateau is reached, the gas levels will only begin to decrease at the rate that the Porta Sens is pulling fresh air through the system, which is relatively small. As can be seen in Table 1, coating the chlorine particles significantly reduced the gas output by 4.7× relative to the uncoated chlorine. This beneficially demonstrates nearly 5 times less gas generated using the coated chlorine technology in a solid chlorine and sodium bromide composition for dispensing a bromine biocide.

Example 2

Additional testing was completed to measure gas evolution with modified OSHA gas sampling techniques to better assess safety improvements by reducing bromine gas generation according to the compositions and methods of the present disclosure. The technique for Example 2 was developed due to the maximum measurement threshold of the Porta Sens employed in Example 1. A single solid composition/puck utilized in Example 1 produced enough gas that it nearly reached the maximum threshold of the Porta Sens sensor module. Therefore, to determine the gas output with more pucks present (as would be the case with dispensing quantities of the bromine biocide for commercial applications) a different method was required.

A modified version of OSHA Method ID-101 was used, which is described herein. Air from the chamber (0.2 L/min) was sparged through a 0.1% sulfamic acid solution for 5 minute increments. After completion of each 5 minute time period, the solution was diluted with a mixture of potassium iodide to convert any chlorine to chloride ion, which was then measured directly with Ion Chromatography. The measured amount of chloride ion was back calculated to determine the amount of $Cl_2$ gas production.

In comparison to the dispensing system and measurement described in Example 1, the present methodology in this Example result in pulling more air through the system relative to the Porta Sens, thus perturbing the system. Accordingly, the absolute ppm values between methods are not equivalent. It is fair, however, to compare between two different chemistry systems each subjected to the same test method.

Six pucks of each system (total wt 1.03 lbs) were placed within the dispenser and sprayed on for 2 minutes in the same way as Example 1. The results from this system can be seen below in Table 2. In this system, coating the chlorine pucks reduced the total gas output by 3.2 times compared to the uncoated chlorine control.

TABLE 2

| Time | Coated Chlorine/NaBr | Uncoated Chlorine/NaBr | |
|---|---|---|---|
| 0-5 | 1.19 | 3.45 | |
| 5-10 | 6.87 | 15.2 | |
| 10-15 | 10.9 | 24.9 | |
| 15-20 | 10.9 | 33.9 | |
| 20-25 | 11.3 | 35.7 | |
| 25-30 | 10.7 | 34.5 | |
| 30-35 | 10.7 | 32.5 | |
| 35-40 | 9.86 | 33.1 | Multiplier |
| Average of 3 peak points | 11.0 | 34.7 | 3.2 |

As can be seen in Table 2, coating the chlorine particles significantly reduced the gas output by 3.2× relative to the uncoated chlorine. This beneficially demonstrates at least a 3 times reduction in gas generated using the coated chlorine technology in a solid chlorine and sodium bromide composition for dispensing a bromine biocide. The results of at least a 3 time reduction is gas (even in a system when fresh air is passing through and diluting the gas concentration) which is a key multiplier to show the benefit of the compositions and methods of the invention.

The inventions being thus described, it will be obvious that the same may be varied in many ways. Such variations are not to be regarded as a departure from the spirit and scope of the inventions and all such modifications are intended to be included within the scope of the following claims. The above specification provides a description of the manufacture and use of the disclosed compositions and methods. Since many embodiments can be made without departing from the spirit and scope of the invention, the invention resides in the claims.

What is claimed is:

1. A method of dispensing a biocidal composition comprising:
   providing a solid biocide composition to an external dispenser, wherein the composition comprises from about 70 wt-% to about 99 wt-% of a coated chlorine and from about 1 wt-% to about 30 wt-% of a bromide salt;
   intermittently contacting a water source onto the solid biocide composition through the external dispenser, initiating a reaction between the water source, coated chlorine, and bromide salt at a wet interface on the solid biocide composition; and
   generating an aqueous biocide solution of hypobromous acid and/or hypobromite from the reaction, wherein the aqueous biocide solution carries bromine gas generated by the solid biocide composition into a fluid delivery system, and
   wherein the coated chlorine is chloroisocyanurate or chloroisocyanuric acid, trichloroisocyanuric acid, dichloroisocyanuric acid or salt thereof, coated by a sulfate, tripolyphosphate, or combination thereof, and reduces the concentration of bromine gas generated from the solid biocide composition in the presence of residual water in the external dispenser when the water source is not contacting the solid biocide.

2. The method of claim 1, wherein the coated chlorine has at least about 50% available chlorine in its base chlorine before it is coated.

3. The method of claim 1, wherein the coated chlorine provides a physical barrier between the chlorine and the bromide salt to prevent premature reaction in the dispenser and delays the reaction.

4. The method of claim 3, wherein the reaction is delayed until the solid biocide composition is in contact with water in a dispensing line or a bulk water system.

5. The method of claim 1, wherein the solid biocide composition is a pellet, tablet, lozenge, puck, briquette, brick, or block, and wherein the solid biocide composition is a multi-use solid.

6. The method of claim 1, wherein the solid biocide composition has a weight from about 100 grams to about 10 kilograms.

7. The method of claim 1, wherein the water source is dosed for from about 30 seconds to about 5 minutes.

8. The method of claim 1, wherein the external dispenser is physically separated from a main water system.

9. The method of claim 1, wherein the reduction in concentration of bromine gas is at least about 2 times compared to the concentration of bromine gas generated by a non-coated chlorine reagent.

10. The method of claim 1, wherein the reduction in concentration of bromine gas is at least about 3 times compared to the concentration of bromine gas generated by a non-coated chlorine reagent.

11. The method of claim 1, wherein the reduction in concentration of bromine gas is at least about 5 times compared to the concentration of bromine gas generated by a non-coated chlorine reagent.

12. The method of claim 1, wherein the solution of hypobromous acid and/or hypobromite has pH from about 7 to about 10.

13. The method of claim 1, wherein the coated chlorine comprises from about 85 wt-% to about 99 wt-% of the solid biocide composition and the bromide salt comprises from about 1 wt-% to about 15 wt-% of the solid biocide composition.

* * * * *